United States Patent [19]
Eppler et al.

[11] Patent Number: 6,005,072
[45] Date of Patent: Dec. 21, 1999

[54] PROTEINS CLOSELY RELATED TO OPIOID RECEPTORS

[75] Inventors: Cecil Mark Eppler, Langhorne; Bradley A. Ozenberger, Yardley, both of Pa.; Jeffrey D. Hulmes, Lake Placid, N.Y.

[73] Assignee: American Cyanamid Company, Wayne, N.J.

[21] Appl. No.: 08/454,552

[22] Filed: May 30, 1995

Related U.S. Application Data

[60] Division of application No. PCT/US95/00939, Jan. 20, 1995, which is a continuation-in-part of application No. 08/185,360, Jan. 21, 1994, abandoned.

[51] Int. Cl.[6] .................. C07K 14/705; C12N 15/12
[52] U.S. Cl. .................. 530/350; 435/69.1; 435/252.3; 435/254.11; 435/325; 530/395
[58] Field of Search .................. 530/350, 395; 435/69.1, 325, 252.3, 254.11, 352

[56] References Cited

U.S. PATENT DOCUMENTS

| | | | |
|---|---|---|---|
| 5,242,822 | 9/1993 | Marullo et al. | 435/69.7 |
| 5,389,543 | 2/1995 | Bunzow et al. | 435/69.1 |
| 5,658,783 | 8/1997 | Grandy et al. | 435/325 |

FOREIGN PATENT DOCUMENTS

WO95/19986   7/1995   WIPO.

OTHER PUBLICATIONS

Wang, J.B., et al. (1983) "μ Opiate Receptor: cDNA cloning and Expression", *Proc. Natl. Acad. Sci., USA*, vol. 90, pp. 10230–10234.
Y. Chen, et al. (1993) "Molecular Cloning and Functional Expression of a μ–Opioid Receptor from Rat Brain", *Mol. Pharmacol.* 44:8–12.
K. Yasuda (1993), "Cloning and functional comparison of k and s opioid receptors from mouse brain", 90:6736–6740.
B. L. Keiffer (1992), "The S–opioid receptor: isolation of a cDNA by expression cloning and Pharmacological Characterization", 89:12048–12052.
C. J. Evans et al. (1992), "Cloning of a Delta Opioid Receptor by Functional Expression", *Science* 258:1952–1955.
Bruno et al. (1992), "Molecular cloning and Funcational expression of a brain specific somatostatin receptor" *P.N.A.S., USA*, 89:11151–11155.
Chen et al., "Molecular Cloning, Tissue Distribution and Chromosomal Localization of a Novel member of the Opioid Receptor Gene Family", *FEBS Letters*, 347:279–283; 280–281.
Wick et al. (1993), "Isolation of a Novel cDNA Encoding a Putative Member Receptor with High Homology to the Cloned μ, δ and κ Opioid Receptors" *Molecular Brain Research*, 27:37–44; 39–43.
Coscia et al. (1991), "A Monoclonal Anti–idiotypic Antibody to μ, and δ Opioid Receptors", *Molecular Brain Research* 9:299–306; 300–303.

Jaffe et al., *The Pharmacological Basis of Therapeutics*, 22:491–531, 1985.
Goldstein et al., *Opiods: Past, Present and Future*, 10:127–143, 1984.
Lord et al., *Nature*, 267:495–499, 1977.
Schulz et al., *J. Pharmacol. Exp. Ther.*, 216:604–606, 1981.
Loh et al., *Ann. Rev. Pharmacol. Toxicol.*, 30:123–147, 1990.
Birnbaumer et al., *Biochem. Biophys. Acta.*, 1031:163–224, 1990.
Bidlack et al., *PNAS USA*, 78:636–639, 1981.
Gioannini et al., *J. Biol. Chem.*, 260:15117–15121, 1985.
Maneckjee et al., *PNAS USA*, 82:594–598, 1985.
Cho et al., *PNAS USA*, 83:4138–4149, 1986.
Ueda et al., *Neurosci. Lett*, 75:339–344, 1987.
Simon et al., *Neuropeptides*, 75:339–344, 1987.
Ahmed et al., *Life Sciences*, 44:861–871, 1989.
Laemmli et al., *Nature*, 227:680–685, 1970.
Whithead et al., *Nature*, 305:158–159, 1983.
Merril et al., *Science*, 211:1437–1438, 1981.
Wessel et al., *Anal. Bioch.*, 138:141–143, 1984.
Blume et al., *PNAS USA*, 75:1713–1717, 1978.
Childers et al., *Life Sciences*, 23:759–762, 1978.
Yinchang et al., *Proc. CAMS and PUMC*, 4:1–7, 1989.
Schofield et al., *EMBO J.*, 8:489–495, 1989.
Bidlack et al., *J. Biol. Chem.*, 261:15844–15849, 1989.
Bidlack et al., *J. Biol. Chem.*, 260:15655–15661, 1991.
Roy et al., *BBRC*, 150:237–244, 1988.
Roy et al., *BBRC*, 154:688–693, 1988.
Xie et al., *PNAS USA*, 89:4124–4128, 1992.
Libert et al., *Science*, 244:569–572, 1989.
Chow et al., *Mol. Pharmacol.*, 24:203–212, 1983.
Sambrook et al. (1989), *Molecular Cloning*, 2nd Ed., p. 163.
Ueda et al. (1988), "Reconstitution of rat brain μ opioid receptors . . . ", *P.N.A.S.* 85:7013–7017.
Jin et al. (1983), "Solubilization and purification of opioid receptor . . . ", abstract of *Proc. Chin. Med. Acad. Perking Union Medical Coll.* 4:(1):1–7.
Bunzow et al., FEBS Letters, 347, 284–288, 1994.
Fukuda et al., FEBS Letters, 343, 42–46, 1994.

*Primary Examiner*—Sally P. Teng
*Attorney, Agent, or Firm*—Darby & Darby

[57] ABSTRACT

Isolated DNAs encoding opiorph receptor polypeptides are provided. Recombinant cloning vectors which include these DNA sequences and cells which include these vectors are also provided. Methods for detecting the expression, in a tissue, of mRNA encoding a polypeptide encoded by this DNA are encompassed as well as methods for producing these polypeptides. These isolated polypeptides and antibodies to these polypeptides are also contemplated.

3 Claims, 11 Drawing Sheets

FIG. 1A

```
GCGGCCGCCT TTCTGCTAAG CATTGGGGTC TATTTGGCC CAGCTTCTGA AGAGGCTGTG     60
TGTGCCGTTG GAGGAACTGT ACTGAGTGGC TTTGCAGGGT GACAGCATGG AGTCCCTCTT   120
TCCTGCTCCA TACTGGGAGG TCTTGTATGG CAGCCACTTT CAAGGGAACC TGTCCCTCCT   180
AAATGAGACC GTACCCCACC ACCTGCTCCT CAATGCTAGT CACAGCGCCT TCCTGCCCCT   240
TGGACTCAAG GTCACCATCG TGGGCTCTA CTTGGCTGTG TGCATCGGGG GGCTCCTGGG   300
GAACTGCCTC GTCATGTATG TCATCCCTCAG GCACACCAAG ATGAAGACAG CTACCAACAT   360
TTACATATTT AATCTGGCAC TGGCTGATAC CCTGGTCTTG CTAACACTGC CCTTCCAGGG   420
CACAGACATC CTACTGGGCT TCTGGCCATT TGGGAATGCA CTCTGCAAGA CTGTCATTGC   480
TATCGACTAC TACAAACATG TTTTACTCTG ACCGCCATGA GCGTAGACCG   540
CTATGTGGCT ATCTGCCACC CTATCCGTGC CCTTGATGTT CGGACATCCA GCAAAGCCCA   600
GGCTGTTAAT GTGGCCATAT GGGCCCTGGC TTCAGTGGTT GGTGTTCCTG TTGCCATCAT   660
GGGTTCAGCA CAAGTGGAAG ATGAAGAGAT CGAGTGCCTG GTGGAGATCC CTGCCCCTCA   720
GGACTATTGG GGCCCTGTAT TCGCCATCTG CATCTTCCTT TTTTCCTTCA TCATCCCTGT   780
```

FIG. 1B

```
GCTGATCATC TCTGTCTGCT ACAGCCTCAT GATTCGACGA CTTCGTGGTG TCCGTCTGCT    840
TTCAGGCTCC CGGGAGAAGG ACCGAAACCT GCGGCGTATC ACTCGACTGG TGCTGGTAGT    900
GGTGGCTGTG TTTGTGGGCT GCTGGACGCC TGTGCAGGTG TTTGTCCTGG TTCAAGGACT    960
GGGTGTTCAG CCAGGTAGTG AGACTGCAGT TGCCATCCTG CGCTTCTGCA CAGCCCCTGGG  1020
CTATGTCAAC AGTTGTCTCA ATCCCATTCT CTATGCTTTC CTGCACCCGG GAGATGCAGG   1080
CTGCTTTAGA AAGTTCTGCT GTGCTTCATC CCTGCACCGG TGGTTGCAAG ACTTCTGAGA   1140
TGTGCGGAGC ATTGCCAAGG ATGTTGGCCT TGGTTGCAAG ACTTCTGAGA CAGTACCACG   1200
GCCAGCATGA CTAGGCGTGG ACCTGCCCAT GGTGCCTGTC AGCCCACAGA GCCCATCTAC   1260
ACCCAACACG GAGCTCACAC AGTCACTGC TCTCCTAGGTT GACCCTGAAC CTTGAGCATC   1320
TGGAGCCTTG AATGGCTTTT CTTTTGGATC AGGATGCTCA GTCCTAGAGG AAGACCTTTT   1380
AGCACCATGG GACAGGTCAA AGCATCAAGG TGGTCTCCAT GGCCTCTGTC AGATTAAGTT   1440
CCCTCCCCTGG TATAGGACCA GAGAGGACCA AAGGAACTGA ATAGAAACAT CCACAACACA  1500
```

FIG. IC

```
GTGGACATGC CTGGTGAGCC CATGTAGGTA TTCATGCTTC ACTTGACTCT TCTCTGGCTT    1560
CTCCCTGCTG CCCTGGCTCT AGCTGGGCTC AACCTGAGGT ATTGTAGTGG TCATGTAGTC    1620
ACTCTTGTGA CTACATGTTG TGTGCTGTTG CTCTCGGCCT TTCAGTATTT CCACAGGACT    1680
GCTGAACATA CCTGGTATTG CAGTGGGGAG CATTAATTTT CTTTTAAAGT GAGACTGGCC    1740
CTTAAGCTTG GCGTTGCCTT GGAGCGTCTT CTACTTCTGA CTTCACTGAT GCAGTCAGAT    1800
TACCCGAGGG TGAGCATCAG TGGTTTCTTG GATGGCTGTT TTCTGAAGAT TCTTCCCATC    1860
CAGTACATGG AGTCTATGAA GGGGAGTCAC AATTCATCTG GTACTGCCAC TACCTGCTCT    1920
ATAATCCTGG GCTATCTTCT TGGCAAGATG ACAGTGGGGG AGACAAGACA CAGAGCTTCC    1980
CTAAGGCTCT TTCCCTCCAA AACCACTGTG AACTCTTATC CTACAGACTG TTCGGCAAGC    2040
ACTGCTTCTA GGTGTGTGGG AGGTAATCAG GAGAAAGCTT TGTGGCCTCT GTAGGCTGCT    2100
```

FIG. 1D

| | |
|---|---|
| CACAACATGG AGGCACCACA TGCTGGTCTT GCCTGCTTAG TACAGGCAGG ACAGAGCAGA | 2160 |
| ATATGCTCTC TCTCGATTCT CTACAAACTC CCTCAGTTCT CCAGCAGAGT CTCTTTTACT | 2220 |
| TGCTATCAGA GGTCAGGAGT TGTACTGCTA GAAGCATACT TGTAGCTTGG GAAGAGTGGC | 2280 |
| AGTCAGGATG TGTTCTACTC TATATCCACA GTGACCACCT GCTTCATATA TAGGGTTAGG | 2340 |
| ACATATCTGA GTAAGGCCTG AGTGTGCTGC CAAATTGGAG GTTGGTATGA GAGCTGATGC | 2400 |
| CTAAAGTGGC TCATTTGCAA GGACTATTAT GGTTTGGAAT AGCAATGGGG GGCATGGGAA | 2460 |
| GAAGAGTCTA TACCTTGGAG ATCTATTTGA TGGTTCACAG AAGAGGTTTT GTAAACGCCC | 2520 |
| TTTCTATGGG TCAGATATCA AAATACCAGC AACGTTGGAT AGATTCTGAC CTTTTACTGA | 2580 |
| GACCTCGGTC AGATGGTTTC ATGTCATGCA GAGAACCTAG GCTGGTTCCT GTGTCAGAGA | 2640 |
| GACCTGGGCT TCTGGGGAGG CCAGGGTTCT TCCTTTGACA CTTGTGCGGG AGCCGTTAGC | 2700 |
| TCTAGA | 2706 |

FIG. 2

MESLFPAPYW EVLYGSHFQG NLSLLNETVP HHLLLNASHS AFLPLGLKVT
IVGLYLAVCI GGILGNCLVM YVILRHTKMK

TATNIYIFNL ALADTLVLLT LPFQGTDILL GFWPFGNALC KTVIAIDYYN
MFTSTFTLTA MSVDRYVAIC HPIRALDVRT

SSKAQAVNVA IWALASVVGV PVAIMGSAQV EDEEIECLVE IPAPQDYWGP
VFAICIFLFS FIIPVLIISV CYSLMIRRLR

GVRLLSGSRE KDRNLRRITR LVLVVVAVFV GCWTPVQVFV LVQGLGVQPG
SETAVAILRF CTALGYVNSC LNPILYAFLD

ENFKACFRKF CCASSLHREM QVSDRVRSIA KDVGLGCKTS ETVPRPA

FIG. 3A

```
                1                                                           #   50
rXor1       ..........  ..........  ..........  .....MESLF  PAPYWEVLYG  SHFQGNLSLL
rMor1       MDSSTGPGNT  SDCSDPLAQA  SCSPAPGSWL  NLSHVDGNQS  DPCGLNRTGL
rDor1       ..........  ......MEPV  PSARAE...L  QFSLL.ANVS  DTFPSAFPSA
rKor1       ..........  ..MESPIQIF  RGEPGPTCAP  SACLLPN...S  SSWFPNWAES
Consensus   ----------  ----------  ----------  ----------  ---------S  ----------

#51                                                #          100
rXor1       NETVPHHLLL  NASHSAFLPL  GLKVTIVGIV  TAVCIGILLG  NCLVMYVILR
rMor1       GGNDSLCPQ.  ...TGSP.SM  VTAITIMALY  SIVCVVGLFG  NFLVMYVIVR
rDor1       SANASGSPG.  ...ARSASSL  ALAIAITALY  SAVCAVGLLG  NVLVMFGIVR
rKor1       DSNGSVGSED  QQLEPAHISP  AIPVIITAVY  SVVFVVGLVG  NSLVMFVIIR
Consensus   --N-S-----  -------S--  ---I-I-A-Y  S-V--VGL-G  N-LVMF-IVR 101                                                            150
rXor1       HTKMKTATNI  YIFNLALADT  LVLLTLPFQG  TDILLGFWPF  GNALCKTVIA
rMor1       YTKMKTATNI  YIFNLALADA  LATSTLPFQS  VNYLMGTWPF  GTILCKIVIS
rDor1       YTKLKTATNI  YIFNLALADA  LATSTLPFQS  AKYLMETWPF  GELLCKAVLS
rKor1       YTKMKTATNI  YIFNLALADA  LVTTMPFQS   AVYLMNSWPF  GDVLCKIVIS
Consensus   YTKMKTATNI  YIFNLALADA  L-T-TLPFQS  --YLM--WPF  G---LCK-V-S
```

FIG. 3B

```
         151                                                         200
rXorl    IDYYNMFTST FTLTMMSVDR YVAICHPIRA LDVRTSSKAQ AVNVATWALA
rMorl    IDYYNMFTSI FTLCTMSVDR YIAVCHPVKA LDFRTPRNAK IVNVCNWILS
rDorl    IDYYNMFTSI FTLTMMSVDR YIAVCHPVKA LDFRTPAKAK LINICIWVLA
rKorl    IDYYNMFTSI FTLTMMSVDR YIAVCHPVKA LDFRTPLKAK IINICIWLLA
Consensus IDYYNMFTSI FTL--MSVDR YIAVCHPVKA LDFRTP--AK -INIC-W-L-

201                    #                                    250
                         GQWVLLPDSLVSHGFLLVPLPPNPSPA
rXorl    SVVGVPVAIM GSAQVED..E EIECLVEIPA PQ..DYWGPVF AICTFLFSFI
rMorl    SAIGLPVMFM ATTKYRQ..G SIDCTLTFSH PTW.YWENLL KICVFIFAFI
rDorl    SGVGVPIMVM AVTQPRD..G AVVCTLQFPS PSW.YWDTVT KICVFLFAFV
rKorl    SSVGISAIVL GGTKVREDVD VIECSLQFPD DEYSWWDLFM KICVFVFAFV
Consensus S-VG-----M --T----R--- --I--C-L-F-- --W-YWD---- KICVF-FAFV 251                                                         300
rXorl    IPVLIISVCY SLMIRRLRGV RLLSGSREKD RNLRRITRLV LVVVAVFVGC
rMorl    MPVLIITVCY GLMILRLRSV RMLSGSKEKD RNLRRITRMV LVWAVFIVC
rDorl    VPLIITVCY  GLMLLRLRSV RLLSGSKEKD RSLRRITRMV LVVVGAFVVC
rKorl    IPVLIIIVCY TLMILRLKSV RLLSGSREKD RNLRRITKLV LVVVAVFIIC
Consensus -PVLII-VCY -LM-LRL-SV RLLSGS-EKD R-LRRIT-MV LVVV--FIVC
```

FIG. 3C

```
          301
rXor1     WTPVQVFVLV QGL.GVQPGS ETAVAILRFC TALGYVNSCL NPILYAFLDE
rMor1     WTPIHIYVII KALITI.PET TFQTVSWHFC IALGYTNSCL NPVLYAFLDE
rDor1     WAPIHIFVIV WTLVDINRRD PLVVAALHLC IALGYANSSL NPVLYAFLDE
rKor1     WTPIHIFILV EALGSTSHST A.VLSSYYFC IALGYTNSSL NPVLYAFLDE
Consensus W-PIHIFV-V ---------L -------FC IALGY-NS-L NPVLYAFLDE
                                                           350

351                                              400
rXor1     NFKACFRKFC LLSSLHREMQ VSDRVRSIAK DVGLGCKTSE TVPRPA....
rMor1     NFKRCFREFC IPTSSTIEQQ NSTRVRQNTR EHPSTANTVD RTNHQLENLE
rDor1     NFKRCFRQLC RAPCGGQEPG SLRRPRQATA RERVTACTPS .....DGPG
rKor1     NFKRCFRDFC FPIKMRMERQ STNRVR.NTV QDPASMRDVG GMNKPV....
Consensus NFKRCFR-FC -------E-- ---R-R--T- ---------- ----------
```

1 2 3 4 5 6 7 8 9 10 11 12 13 14 15 16

RNAS

1 = BRAIN
2 = PITUITARY
3 = $GH_4C_1$ CELLS
4 = THYMUS
5 = LUNG
6 = HEART
7 = LIVER

8 = KIDNEY
9 = SPLEEN
10 = STOMACH
11 = MUSCLE
12 = FAT
13 = OVARY
14 = TESTIS

CONTROLS

15 = GENOMIC DNA
16 = NO TEMPLATE 1 2 3 4 5 6 7 8 9 10 11 12 13 14 15 16 17 18 19

6,005,072

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 2706 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (F) TISSUE TYPE: Rat brain (xi) SEQUENCE DESCRIPTION: SEQ ID NO:1:

```
GCGGCCGCCT TTCTGCTAAG CATTGGGGTC TATTTTGGCC CAGCTTCTGA AGAGGCTGTG      60

TGTGCCGTTG GAGGAACTGT ACTGAGTGGC TTTGCAGGGT GACAGCATGG AGTCCCTCTT     120

TCCTGCTCCA TACTGGGAGG TCTTGTATGG CAGCCACTTT CAAGGGAACC TGTCCCTCCT     180

AAATGAGACC GTACCCCACC ACCTGCTCCT CAATGCTAGT CACAGCGCCT TCCTGCCCCT     240

TGGACTCAAG GTCACCATCG TGGGGCTCTA CTTGGCTGTG TGCATCGGGG GGCTCCTGGG     300

GAACTGCCTC GTCATGTATG TCATCCTCAG GCACACCAAG ATGAAGACAG CTACCAACAT     360

TTACATATTT AATCTGGCAC TGGCTGATAC CCTGGTCTTG CTAACACTGC CCTTCCAGGG     420

CACAGACATC CTACTGGGCT TCTGGCCATT TGGGAATGCA CTCTGCAAGA CTGTCATTGC     480

TATCGACTAC TACAACATGT TTACCAGCAC TTTTACTCTG ACCGCCATGA GCGTAGACCG     540

CTATGTGGCT ATCTGCCACC CTATCCGTGC CCTTGATGTT CGGACATCCA GCAAAGCCCA     600

GGCTGTTAAT GTGGCCATAT GGGCCCTGGC TTCAGTGGTT GGTGTTCCTG TTGCCATCAT     660

GGGTTCAGCA CAAGTGGAAG ATGAAGAGAT CGAGTGCCTG GTGGAGATCC CTGCCCCTCA     720

GGACTATTGG GGCCCTGTAT TCGCCATCTG CATCTTCCTT TTTTCCTTCA TCATCCCTGT     780

GCTGATCATC TCTGTCTGCT ACAGCCTCAT GATTCGACGA CTTCGTGGTG TCCGTCTGCT     840

TTCAGGCTCC CGGGAGAAGG ACCGAAACCT GCGGCGTATC ACTCGACTGG TGCTGGTAGT     900

GGTGGCTGTG TTTGTGGGCT GCTGGACGCC TGTGCAGGTG TTTGTCCTGG TTCAAGGACT     960

GGGTGTTCAG CCAGGTAGTG AGACTGCAGT TGCCATCCTG CGCTTCTGCA CAGCCCTGGG    1020

CTATGTCAAC AGTTGTCTCA ATCCCATTCT CTATGCTTTC CTGGATGAGA ACTTCAAGGC    1080
```

-continued

```
CTGCTTTAGA AAGTTCTGCT GTGCTTCATC CCTGCACCGG GAGATGCAGG TTTCTGATCG    1140

TGTGCGGAGC ATTGCCAAGG ATGTTGGCCT TGGTTGCAAG ACTTCTGAGA CAGTACCACG    1200

GCCAGCATGA CTAGGCGTGG ACCTGCCCAT GGTGCCTGTC AGCCCACAGA GCCCATCTAC    1260

ACCCAACACG GAGCTCACAC AGGTCACTGC TCTCTAGGTT GACCCTGAAC CTTGAGCATC    1320

TGGAGCCTTG AATGGCTTTT CTTTTGGATC AGGATGCTCA GTCCTAGAGG AAGACCTTTT    1380

AGCACCATGG GACAGGTCAA AGCATCAAGG TGGTCTCCAT GGCCTCTGTC AGATTAAGTT    1440

CCCTCCCTGG TATAGGACCA GAGAGGACCA AAGGAACTGA ATAGAAACAT CCACAACACA    1500

GTGGACATGC CTGGTGAGCC CATGTAGGTA TTCATGCTTC ACTTGACTCT TCTCTGGCTT    1560

CTCCCTGCTG CCCTGGCTCT AGCTGGGCTC AACCTGAGGT ATTGTAGTGG TCATGTAGTC    1620

ACTCTTGTGA CTACATGTTG TGTGCTGTTG CTCTCGGCCT TTCAGTATTT CCACAGGACT    1680

GCTGAACATA CCTGGTATTG CAGTGGGGAG CATTAATTTT CTTTTAAAGT GAGACTGGCC    1740

CTTAAGCTTG GCGTTGCCTT GGAGCGTCTT CTACTTCTGA CTTCACTGAT GCAGTCAGAT    1800

TACCCGAGGG TGAGCATCAG TGGTTTCTTG GATGGCTGTT TTCTGAAGAT TCTTCCCATC    1860

CAGTACATGG AGTCTATGAA GGGGAGTCAC AATTCATCTG GTACTGCCAC TACCTGCTCT    1920

ATAATCCTGG GCTATCTTCT TGGCAAGATG ACAGTGGGGG AGACAAGACA CAGAGCTTCC    1980

CTAAGGCTCT TTCCCTCCAA AACCACTGTG AACTCTTATC CTACAGACTG TTCGGCAAGC    2040

ACTGCTTCTA GGTGTGTGGG AGGTAATCAG GAGAAAGCTT TGTGGCCTCT GTAGGCTGCT    2100

CACAACATGG AGGCACCACA TGCTGGTCTT GCCTGCTTAG TACAGGCAGG ACAGAGCAGA    2160

ATATGCTCTC TCTCGATTCT CTACAAACTC CCTCAGTTCT CCAGCAGAGT CTCTTTTACT    2220

TGCTATCAGA GGTCAGGAGT TGTACTGCTA AAGCATACT TGTAGCTTGG AAGAGTGGC     2280

AGTCAGGATG TGTTCTACTC TATATCCACA GTGACCACCT GCTTCATATA TAGGGTTAGG    2340

ACATATCTGA GTAAGGCCTG AGTGTGCTGC CAAATTGGAG GTTGGTATGA GAGCTGATGC    2400

CTAAAGTGGC TCATTTGCAA GGACTATTAT GGTTTGGAAT AGCAATGGGG GGCATGGGAA    2460

GAAGAGTCTA TACCTTGGAG ATCTATTTGA TGGTTCACAG AAGAGGTTTT GTAAACGCCC    2520

TTTCTATGGG TCAGATATCA AAATACCAGC AACGTTGGAT AGATTCTGAC CTTTTACTGA    2580

GACCTCGGTC AGATGGTTTC ATGTCATGCA GAGAACCTAG GCTGGTTCCT GTGTCAGAGA    2640

GACCTGGGCT TCTGGGGAGG CCAGGGTTCT TCCTTTGACA CTTGTGCGGG AGCCGTTAGC    2700

TCTAGA                                                              2706
```

(2) INFORMATION FOR SEQ ID NO:2:

(i) SEQUENCE CHARACTERISTICS:
        (A) LENGTH: 367 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Rat (xi) SEQUENCE DESCRIPTION: SEQ ID NO:2:

```
Met Glu Ser Leu Phe Pro Ala Pro Tyr Trp Glu Val Leu Tyr Gly Ser
 1               5                  10                  15

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45
```

```
Val Thr Ile Val Gly Leu Tyr Leu Ala Val Cys Ile Gly Gly Leu Leu
     50                  55                  60

Gly Asn Cys Leu Val Met Tyr Val Ile Leu Arg His Thr Lys Met Lys
 65                  70                  75                  80

Thr Ala Thr Asn Ile Tyr Ile Phe Asn Leu Ala Leu Ala Asp Thr Leu
                 85                  90                  95

Val Leu Leu Thr Leu Pro Phe Gln Gly Thr Asp Ile Leu Leu Gly Phe
                100                 105                 110

Trp Pro Phe Gly Asn Ala Leu Cys Lys Thr Val Ile Ala Ile Asp Tyr
            115                 120                 125

Tyr Asn Met Phe Thr Ser Thr Phe Thr Leu Thr Ala Met Ser Val Asp
        130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
            180                 185                 190

Glu Glu Ile Glu Cys Leu Val Glu Ile Pro Ala Pro Gln Asp Tyr Trp
        195                 200                 205

Gly Pro Val Phe Ala Ile Cys Ile Phe Leu Phe Ser Phe Ile Ile Pro
    210                 215                 220

Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
            260                 265                 270

Trp Thr Pro Val Gln Val Phe Val Leu Val Gln Gly Leu Gly Val Gln
        275                 280                 285

Pro Gly Ser Glu Thr Ala Val Ala Ile Leu Arg Phe Cys Thr Ala Leu
    290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ser Leu
                325                 330                 335

His Arg Glu Met Gln Val Ser Asp Arg Val Arg Ser Ile Ala Lys Asp
            340                 345                 350

Val Gly Leu Gly Cys Lys Thr Ser Glu Thr Val Pro Arg Pro Ala
                355                 360                 365
```

(2) INFORMATION FOR SEQ ID NO:3:

(i) SEQUENCE CHARACTERISTICS:
        (A) LENGTH: 391 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Rat (xi) SEQUENCE DESCRIPTION: SEQ ID NO:3:

```
Met Asp Ser Ser Thr Gly Pro Gly Asn Thr Ser Asp Cys Ser Asp Pro
 1               5                  10                  15
```

```
Leu Ala Gln Ala Ser Cys Ser Pro Ala Pro Gly Ser Trp Leu Asn Leu
         20                  25                  30

Ser His Val Asp Gly Asn Gln Ser Asp Pro Cys Gly Leu Asn Arg Thr
         35                  40                  45

Gly Leu Gly Gly Asn Asp Ser Leu Cys Pro Gln Thr Gly Ser Pro Ser
 50                  55                  60

Met Val Thr Ala Ile Thr Ile Met Ala Leu Tyr Ser Ile Val Cys Val
 65                  70                  75                  80

Val Gly Leu Phe Gly Asn Phe Leu Val Met Tyr Val Ile Val Arg Tyr
                 85                  90                  95

Thr Lys Met Lys Thr Ala Thr Asn Ile Tyr Ile Phe Asn Leu Ala Leu
             100                 105                 110

Ala Asp Ala Leu Ala Thr Ser Thr Leu Pro Phe Gln Ser Val Asn Tyr
             115                 120                 125

Leu Met Gly Thr Trp Pro Phe Gly Thr Ile Leu Cys Lys Ile Val Ile
         130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                 165                 170                 175

Asp Phe Arg Thr Pro Arg Asn Ala Lys Ile Val Asn Val Cys Asn Trp
             180                 185                 190

Ile Leu Ser Ser Ala Ile Gly Leu Pro Val Met Phe Met Ala Thr Thr
         195                 200                 205

Lys Tyr Arg Gln Gly Ser Ile Asp Cys Thr Leu Thr Phe Ser His Pro
         210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                 245                 250                 255

Leu Arg Leu Lys Ser Val Arg Met Leu Ser Gly Ser Lys Glu Lys Asp
             260                 265                 270

Arg Asn Leu Arg Arg Ile Thr Arg Met Val Leu Val Val Val Ala Val
         275                 280                 285

Phe Ile Val Cys Trp Thr Pro Ile His Ile Tyr Val Ile Ile Lys Ala
         290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                 325                 330                 335

Ala Phe Leu Asp Glu Asn Phe Lys Arg Cys Phe Arg Glu Phe Cys Ile
             340                 345                 350

Pro Thr Ser Ser Thr Ile Glu Gln Gln Asn Ser Thr Arg Val Arg Gln
             355                 360                 365

Asn Thr Arg Glu His Pro Ser Thr Ala Asn Thr Val Asp Arg Thr Asn
370                 375                 380

His Gln Leu Glu Asn Leu Glu
385                 390
```

(2) INFORMATION FOR SEQ ID NO:4:

(i) SEQUENCE CHARACTERISTICS:
        (A) LENGTH: 367 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
         (A) ORGANISM: Rat (xi) SEQUENCE DESCRIPTION: SEQ ID NO:4:

Met Glu Pro Val Pro Ser Ala Arg Ala Glu Leu Gln Phe Ser Leu Leu
    1               5                   10                  15

Ala Asn Val Ser Asp Thr Phe Pro Ser Ala Phe Pro Ser Ala Ser Ala
                    20                  25                  30

Asn Ala Ser Gly Ser Pro Gly Ala Arg Ser Ala Ser Ser Leu Ala Leu
                35                  40                  45

Ala Ile Ala Ile Thr Ala Leu Tyr Ser Ala Val Cys Ala Val Gly Leu
    50                  55                  60

Leu Gly Asn Val Leu Val Met Phe Gly Ile Val Arg Tyr Thr Lys Leu
    65                  70                  75                  80

Lys Thr Ala Thr Asn Ile Tyr Ile Phe Asn Leu Ala Leu Ala Asp Ala
                    85                  90                  95

Leu Ala Thr Ser Thr Leu Pro Phe Gln Ser Ala Lys Tyr Leu Met Glu
                    100                 105                 110

Thr Trp Pro Phe Gly Glu Leu Leu Cys Lys Ala Val Leu Ser Ile Asp
                    115                 120                 125

Tyr Tyr Asn Met Phe Thr Ser Ile Phe Thr Leu Thr Met Met Ser Val
                    130                 135                 140

Asp Arg Tyr Ile Ala Val Cys His Pro Val Lys Ala Leu Asp Phe Arg
    145                 150                 155                 160

Thr Pro Ala Lys Ala Lys Leu Ile Asn Ile Cys Ile Trp Val Leu Ala
                    165                 170                 175

Ser Gly Val Gly Val Pro Ile Met Val Met Ala Val Thr Gln Pro Arg
                    180                 185                 190

Asp Gly Ala Val Val Cys Thr Leu Gln Phe Pro Ser Pro Ser Trp Tyr
                    195                 200                 205

Trp Asp Thr Val Thr Lys Ile Cys Val Phe Leu Phe Ala Phe Val Val
                    210                 215                 220

Pro Ile Leu Ile Ile Thr Val Cys Tyr Gly Leu Met Leu Leu Arg Leu
    225                 230                 235                 240

Arg Ser Val Arg Leu Leu Ser Gly Ser Lys Glu Lys Asp Arg Ser Leu
                    245                 250                 255

Arg Arg Ile Thr Arg Met Val Leu Val Val Val Gly Ala Phe Val Val
                    260                 265                 270

Cys Trp Ala Pro Ile His Ile Phe Val Ile Val Trp Thr Leu Val Asp
                    275                 280                 285

Ile Asn Arg Arg Asp Pro Leu Val Val Ala Ala Leu His Leu Cys Ile
                    290                 295                 300

Ala Leu Gly Tyr Ala Asn Ser Ser Leu Asn Pro Val Leu Tyr Ala Phe
    305                 310                 315                 320

Leu Asp Glu Asn Phe Lys Arg Cys Phe Arg Gln Leu Cys Arg Ala Pro
                    325                 330                 335

Cys Gly Gly Gln Glu Pro Gly Ser Leu Arg Arg Pro Arg Gln Ala Thr
                    340                 345                 350

Ala Arg Glu Arg Val Thr Ala Cys Thr Pro Ser Asp Gly Pro Gly
                    355                 360                 365

(2) INFORMATION FOR SEQ ID NO:5:

(i) SEQUENCE CHARACTERISTICS:
        (A) LENGTH: 330 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Rat (xi) SEQUENCE DESCRIPTION: SEQ ID NO:5:

```
Met Glu Ser Pro Ile Gln Ile Phe Arg Gly Glu Pro Gly Pro Thr Cys
  1               5                  10                  15

Ala Pro Ser Ala Cys Leu Leu Pro Asn Ser Ser Ser Trp Phe Pro Asn
             20                  25                  30

Trp Ala Glu Ser Asp Ser Asn Gly Ser Val Gly Ser Glu Asp Gln Gln
         35                  40                  45

Leu Glu Pro Ala His Ile Ser Pro Ala Ile Pro Val Ile Ile Thr Ala
 50                  55                  60

Val Tyr Ser Val Val Phe Val Val Gly Leu Val Gly Asn Ser Leu Val
 65                  70                  75                  80

Met Phe Val Ile Ile Arg Tyr Thr Lys Met Lys Thr Ala Thr Asn Ile
                 85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
        115                 120                 125

Val Leu Cys Lys Ile Val Ile Ser Ser Ser Val Gly Ile Ser Ala Ile
130                 135                 140

Val Leu Gly Gly Thr Lys Val Arg Glu Asp Val Asp Val Ile Glu Cys
145                 150                 155                 160

Ser Leu Gln Phe Pro Asp Asp Glu Tyr Ser Trp Trp Asp Leu Phe Met
                165                 170                 175

Lys Ile Cys Val Phe Val Phe Ala Phe Val Ile Pro Val Leu Ile Ile
            180                 185                 190

Ile Val Cys Tyr Thr Leu Met Ile Leu Arg Leu Lys Ser Val Arg Leu
        195                 200                 205

Leu Ser Gly Ser Arg Glu Lys Asp Arg Asn Leu Arg Arg Ile Thr Lys
210                 215                 220

Leu Val Leu Val Val Val Ala Val Phe Ile Ile Cys Trp Thr Pro Ile
225                 230                 235                 240

His Ile Phe Ile Leu Val Glu Ala Leu Gly Ser Thr Ser His Ser Thr
                245                 250                 255

Ala Val Leu Ser Ser Tyr Tyr Phe Cys Ile Ala Leu Gly Tyr Thr Asn
            260                 265                 270

Ser Ser Leu Asn Pro Val Leu Tyr Ala Phe Leu Asp Glu Asn Phe Lys
        275                 280                 285

Arg Cys Phe Arg Asp Phe Cys Phe Pro Ile Lys Met Arg Met Glu Arg
        290                 295                 300

Gln Ser Thr Asn Arg Val Arg Asn Thr Val Gln Asp Pro Ala Ser Met
305                 310                 315                 320

Arg Asp Val Gly Gly Met Asn Lys Pro Val
                325                 330
```

(2) INFORMATION FOR SEQ ID NO:6:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal fragment (vi) ORIGINAL SOURCE:
        (A) ORGANISM: Rat (xi) SEQUENCE DESCRIPTION: SEQ ID NO:6:

Gly Gln Trp Val Val Leu Leu Pro Asp Ser Leu Val Ser His Gly Phe
1             5                    10             15

Leu Leu Val Pro Leu Pro Pro Asn Pro Ser Pro Ala
           20                25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(xi) SEQUENCE DESCRIPTION: SEQ ID NO:7:

ACGATGAAGC ACTGAGCCAC CACCA                                         25

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (v) FRAGMENT TYPE: internal (vi) ORIGINAL SOURCE:
        (F) TISSUE TYPE: rat brain (xi) SEQUENCE DESCRIPTION: SEQ ID NO:8:

Val Leu Val Val Val Ala Val Phe Ile Val
1             5                  10

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(xi) SEQUENCE DESCRIPTION: SEQ ID NO:9:

CTTCAATCCT GGCTCTTGCC TGAT                                          24

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER corresponding to
            nucleotides 51 to 71 of SEQ ID NO:1"

(xi) SEQUENCE DESCRIPTION: SEQ ID NO:10:

AGGGCACAGA CATCCTACTG G                                        21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER corresponding to
            nucleotides 546-566 of SEQ ID NO:1"

(xi) SEQUENCE DESCRIPTION: SEQ ID NO:11:

AGCCTGAAAG CAGACGGACA C                                        21

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(xi) SEQUENCE DESCRIPTION: SEQ ID NO:12:

ACCCTGGTCT TGCTAACA                                              18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(xi) SEQUENCE DESCRIPTION: SEQ ID NO:13:

CAGCACCAGT CGAGTGAT                                              18

PROTEINS CLOSELY RELATED TO OPIOID RECEPTORS

This application is a divisional application of co-pending International Application No. PCT/US95/00939, filed Jan. 20, 1995, which is a continuation-in-part of U.S. patent application Ser. No. 08/185,360, filed Jan. 21, 1994, now abandoned.

FIELD OF THE INVENTION

This invention pertains to DNA sequences that encode opiorph receptor polypeptide(s). Opiorph receptor polypeptides are highly related to known opioid receptors. The invention also encompasses the opiorph receptors and antibodies directed against these polypeptides.

BACKGROUND TO THE INVENTION

Opioid receptors are members of the receptor superfamily of polypeptides that typically have seven transmembrane domains and that are functionally coupled to G proteins. cDNAs encoding several types of opioid receptors have been cloned, including the mu, delta, and kappa opioid receptors (Wang et al., (1983), *Proc. Natl. Acad. Sci., USA*, 90:10230; Chen et al., (1993), *Mol. Pharmacol.*, 44:8; Evans et al., (1992), *Science*, 258:1952; Kieffer et al., *Proc. Natl. Acad. Sci., USA*, 89:12048; Yasuda et al, (1993), *Proc. Natl. Acad. Sci., USA*, 90:6736.)

It is believed that the proteins encoded by these cDNAs mediate many of the physiological effects of endogenous opioid agonist peptides, such as, for example, met- and leu-enkephalin, beta-endorphin, and dynorphin, as well as opiate alkaloids such as morphine (Jaffe and Martin, in *The Pharmacological Basis of Therapeutics*, A. G. Gilman et al., eds., MacMillan, N.Y., 1985, pages 491–531). These physiological effects, which occur in both the central and peripheral nervous system, include analgesia, drowsiness, mood changes, respiratory depression, decreased gastrointestinal mobility, nausea, vomiting, and other alterations in the endocrine and autonomic nervous system.

Another family of opioid receptors, the epsilon receptors, have been studied in brain and immune tissue (Nock et al., (1993), *J. Pharm. Expl. Therap.*, 264:349; Sibinga et al., (1988), *Ann. Rev. Immunol.*, 6:219). Epsilon receptors, in the immune system, appear to mediate the effects of beta-endorphin on the cytotoxicity of monocytes, on conversion of precursor cells into killer cells, and on chemotaxis.

It has been found that some opioid effects may be mediated by receptors other than the known mu, delta, and kappa receptors. This indicates the existence of subtypes of each of these receptor classes. For example, two subtypes of mu-receptor, two subtypes of delta receptor, and three subtypes of kappa receptor have been identified pharmacologically (Pasternak, *Clin.Neuropharm.* 16:1, 1993).

New opioid receptor polypeptides have now been identified by isolating cDNAs that are homologous to known receptors.

BRIEF DESCRIPTION OF THE DRAWINGS

FIG. 1 is an illustration of DNA sequences encoding rat opiorph receptor polypeptides (SEQ ID NO: 1).

FIG. 2 is an illustration of the predicted amino acid sequences of rat opiorph receptor polypeptides (SEQ ID NO: 2).

FIG. 3 illustrates a comparison among an opiorph receptor polypeptide sequence of FIG. 2 (OR7) (rXor1) (SEQ ID NO: 2) and the amino acid sequences of rat delta opioid receptor polypeptide (rDor1) (SEQ ID NO: 4), rat mu opioid receptor polypeptide (rMor1) (SEQ ID NO: 3), and rat kappa opioid receptor polypeptide (rKor1) (SEQ ID NO: 5). Putative transmembrane domains are shaded. The extra amino acids encoded by the large splice variant of the opiorph receptor polypeptides are shown as an insert (SEQ ID NO: 6).

SUMMARY OF THE INVENTION

Figure 4:
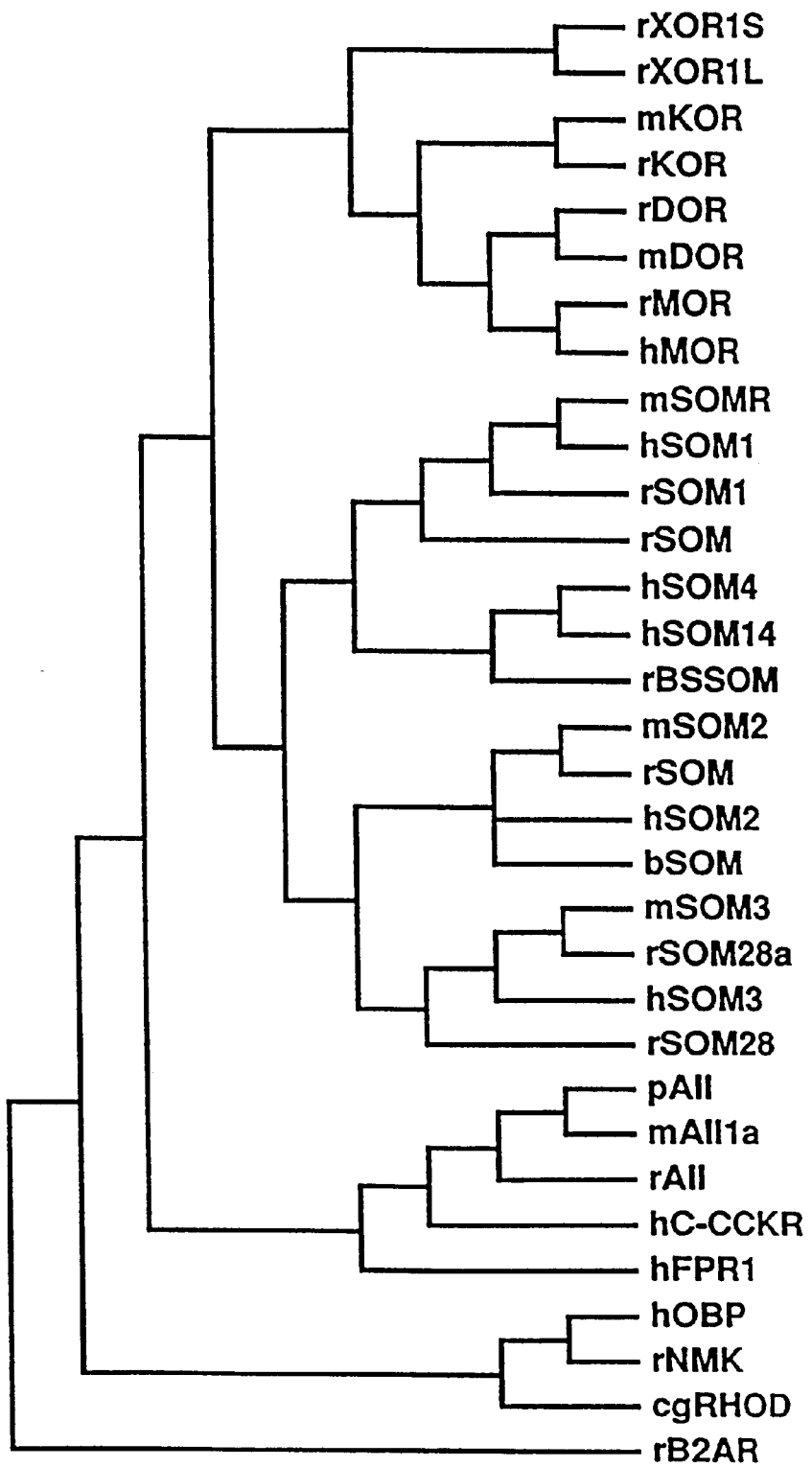
FIG. 4 is a dendrogram illustrating the evolutionary relatedness of the opiorph receptor polypeptides of FIG. 2 and other G-protein-linked receptor polypeptides.

Isolated DNAs encoding opiorph receptor polypeptides are provided. These DNAs include:

(A) nucleotides 367–918 of the DNA sequence of FIG. 1 (SEQ ID NO: 1);

(B) nucleotides 368–916 of the DNA sequence of FIG. 1 (SEQ ID NO: 1);

(C) DNA encoding amino acid residues 88–269 of the amino acid sequence of FIG. 2 (SEQ ID NO: 2);

(D) sequence-conservative variants, function-conservative variants, and sequence- and function-conservative variants of any of (A), (B), or (C);

(E) intronless DNA encoding an amino acid sequence selected from the group consisting of amino acid residues 88–269 of the amino acid sequence of FIG. 2 (SEQ ID NO: 2) and function-conservative variants thereof; and (F) DNA wherein exons of the DNA encode an amino acid sequence selected from the group consisting of amino acid residues 88–269 of the amino acid sequence of FIG. 2 (SEQ ID NO: 2) and function-conservative variants thereof.

Recombinant cloning vectors comprising these DNA sequences and cells comprising these vectors are provided as well.

Also contemplated by the present invention are methods for detecting the expression, in a tissue, of mRNA encoding a polypeptide having an amino acid sequence selected from the group consisting of amino acid residues 88–269 of the amino acid sequence of FIG. 2 (SEQ ID NO: 2) and function-conservative variants thereof. These methods comprise:

(A) selecting at least one oligonucleotide sequence unique to the polypeptide, wherein the sequence comprises from about 15 to about 30 nucleotides;

(B) synthesizing the oligonucleotides;

(C) hybridizing the oligonucleotide to total mRNA isolated from the tissue under stringent conditions; and (D) detecting the hybridization.

Further contemplated are methods for producing a polypeptide selected form the group consisting of amino acid residues 88–269 of the amino acid sequence of FIG. 2 (SEQ ID NO: 2) and function-conservative variants thereof. These methods include (A) culturing the cells above in a medium and under conditions suitable for expression of the polypeptide;

(B) expressing the polypeptide; and (C) optionally, isolating the expressed polypeptide.

Isolated polypeptides selected from the group consisting of amino acid residues 88–269 of FIG. 2 (SEQ ID NO: 2) and function-conservative variants thereof, as well as antibodies to these polypeptides are also contemplated.

DETAILED DESCRIPTION OF THE INVENTION

DNA has been isolated that encodes opiorph receptor polypeptide(s). These opiorph receptor polypeptide(s) are related to, but distinct from, known opioid receptor polypeptides. The opiorph receptor polypeptide(s) has been characterized, establishing the differences between it and other members of the opioid receptor family. Accordingly, the opiorph receptor polypeptide(s) is an important target for the development of new opioid or opioid-like agonists and antagonists, which are psychotropic, analgesic, anti-emetic, immunomodulatory, growth hormone-releasing, and growth-promoting agents. Agonists or antagonists of the invertebrate homologue(s) of the opiorph receptor polypeptide(s) are believed to be pesticides. The DNA, opiorph receptor polypeptide(s), and antibodies of the present invention can be used, for example, for the detection and manipulation of pharmacological phenomena that are mediated by opioids and opioid-related molecules.

Opiorph Receptor Nucleic Acids

The DNA sequence set forth in FIG. 1 (SEQ ID NO: 1) corresponds to the CDNA sequence encoding the seven transmembrane domain opiorph receptor polypeptide (OR7). The 3.2 kb sequence comprises a 5' untranslated region of 128 bp, an open reading frame of 1,101 bp, and a 3' untranslated region of 2 kb that includes a polyadenylation consensus site. The sequence also includes a splice donor site and a splice acceptor site. When the intervening sequence is excised by splicing, the resulting sequence encodes a smaller form of opiorph receptor polypeptide. The sequence between nucleotides 367 and 918 and preferably between nucleotides 368 and 916 encodes a five transmembrane-domain polypeptide (OR-5) (amino acid residues 8814 269 of FIG. 2 (SEQ ID NO: 2)).

FIG. 2 (SEQ ID NO: 2) illustrates the amino acid sequence of the opiorph receptor polypeptide OR7S (short splice variant), which is encoded by the DNA sequence of FIG. 1 and which includes the sequence of OR5 (amino acid residues 88–269 of FIG. 2) (SEQ ID NO: 1). Because of the degeneracy of the genetic code in that multiple codons encode for certain amino acids, DNA sequences other than that shown in FIG. 1 (SEQ ID NO: 1) can also encode the opiorph amino acid sequences shown in FIG. 2 (SEQ ID NO: 2). Such other DNAs include those containing "sequence-conservative" variation in which a change in one or more nucleotides in a given codon results in no alteration in the amino acid encoded at that position.

Additionally, a given amino acid residue in a polypeptide can be changed without altering the overall conformation and function of the native polypeptide. Such "function-conservative" variants include, but are not limited to, replacement of an amino acid with one having similar physico-chemical properties, such as, for example, acidic, basic, hydrophobic, and the like.

The opiorph receptor(s) DNAs within the scope of the present invention are those of FIG. 1 (SEQ ID NO: 1), sequence-conservative variant DNAs, DNA sequences encoding function-conservative variant polypeptides, and combinations thereof.

Generally, nucleic acid manipulations according to the present invention use methods that are well known in the art, as disclosed in e.g. *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, New York, N.Y., 1992).

The present invention encompasses cDNA and RNA sequences and sense and antisense sequences. The invention also encompasses genomic opiorph receptor polypeptide DNA sequences and flanking sequences, including, but not limited to, regulatory sequences. Nucleic acid sequences encoding opiorph receptor polypeptide(s) may also be associated with heterologous sequences, including promoters, enhancers, response elements, signal sequences, polyadenylation sequences, introns, 5'- and 3'-noncoding regions, and the like. Transcriptional regulatory elements that may be operably linked to opiorph receptor polypeptide DNA sequence(s) include, without limitation, those that have the ability to direct the expression of genes derived from prokaryotic cells, eukaryotic cells, viruses of prokaryotic cells, viruses of eukaryotic cells, and any combination thereof. Other useful heterologous sequences are known to those skilled in the art.

The nucleic acids of the present invention can be modified by methods known to those skilled in the art to alter their stability, solubility, binding affinity, and specificity. For example, the sequences can be selectively methylated. The nucleic acid sequences of the present invention may also be modified with a label capable of providing a detectable signal, either directly or indirectly. Exemplary labels include radioisotopes, fluorescent molecules, biotin, and the like.

Vectors and Transformants

The present invention also provides vectors that include nucleic acids encoding the opiorph receptor polypeptide(s). Such vectors include, for example, plasmid vectors for expression in a variety of eukaryotic and prokaryotic hosts. Preferably, vectors also include a promotor operably linked to the opiorph receptor polypeptide encoding portion. The encoded opiorph receptor polypeptide(s) may be expressed by using any suitable vectors and host cells as explained herein or otherwise known to those skilled in the art.

Vectors will often include one or more replication systems for cloning or expression, one or more markers for selection in the host such as, for example, antibiotic resistance, and one or more expression cassettes. The inserted coding sequences may be synthesized, isolated from natural sources, prepared as hybrids, or the like. Ligation of the coding sequences to the transcriptional regulatory sequences may be achieved by methods known to those skilled in the art. Suitable host cells may be transformed/transfected/infected by any suitable method including electroporation, $CaCl_2$ mediated DNA uptake, fungal infection, microinjection, microprojectile, or the like.

Suitable vectors for use in practicing the present invention include without limitation YEp352, pcDNAI (InVitrogen), and pRC/CMV (InVitrogen). Suitable host cells include *E. coli,* yeast, COS cells, PC12 cells, CHO cells, GH4C1 cells, and amphibian melanophore cells.

Nucleic acids encoding the opiorph receptor polypeptide(s) may also be introduced into cells by recombination events. For example, such a sequence can be microinjected into a cell, effecting homologous recombination at the site of an endogenous gene encoding the polypeptide, an analog or pseudogene thereof, or a sequence with substantial identity to an opiorph receptor polypeptide-encoding gene. Other recombination-based methods such as non-homologous recombinations, and deletion of endogenous gene by homologous recombination, especially in pluripotent cells, may also be used.

Opiorph Receptor Polypeptides

Opiorph receptor polypeptide OR7, including the fragment of OR 7 designated OR5, is shown in FIG. 2 (SEQ ID NO: 2). Sequence analysis using Genetics Computer Group software revealed the presence of an open reading frame encoding 367 amino acids, containing seven candidate hydrophobic membrane-spanning domains of 20–24 amino acids that are homologous to those in other, G-protein-linked transmembrane receptors (see FIGS. 3 (SEQ ID NO: 2), (SEQ ID NO: 3), (SEQ ID NO: 4), (SEQ ID NO: 5) snf (SEQ ID NO: 6) and 4). Additionally, the sequence contains four consensus sequences for asparagine-linked glycosylation, as well as serine and threonine residues that are contained in possible intracellular domains and are present within local sequence contexts favorable for phosphorylation by protein kinases A and C. The smaller polypeptide encoded by the splice variant lacks 28 amino acids (SEQ ID NO: 6), including a glycosylation consensus sequence, but is otherwise identical to the larger polypeptide.

Several features of the OR7 structure are consistent with specific functional 5 implications. The size of the third putative intracellular loop predicted by the CDNA is modest, consistent with sizes of the homologous segments in the seven transmembrane domain receptors that do not couple to adenylate cyclase stimulating G proteins. Although many residues lying in transmembrane regions are conserved, the OR7 sequence (SEQ ID NO: 2) contain a glutamine at position 305 instead of the histidine that lies in comparable positions in the mu, kappa, and delta opiate receptor sequences. The 28 additional amino acids (SEQ ID NO: 6) encoded by the longer splice variant separate a number of negatively charged residues in the putative third extracellular segment from each other.

The present invention also encompasses function-conservative variants as explained above of the amino acid sequences in FIG. 2 (SEQ ID NO: 2). Furthermore, fragments of the polypeptide greater than 20 amino acids in length may also exhibit functional properties characteristic of the intact native molecule, for example, the capacity to bind particular ligands.

Opiorph receptor polypeptides may be isolated from any source, such as, for example, native sources in rat tissues or heterologous cells programmed to produce the polypeptide by recombinant DNA methods. Alternately, the polypeptide(s) or peptide fragments thereof can be synthesized in a cell-free context. Peptides of up to 50 amino acids can be chemically synthesized, and larger polypeptides can be synthesized using cell-free translation systems.

Opiorph receptor polypeptides may be modified by methods known in the art. For example, the polypeptides may be phosphorylated or dephosphorylated, glycosylated or deglycosylated, acylated or deacylated, and the like.

In addition, opiorph receptor polypeptides may be expressed as fusion proteins incorporating heterologous sequences. Appropriate fusion partners include sequences useful for immobilization and purification. For example, sequences derived from glutathione-S-transferase (GSI) provide a binding site for immobilized glutathione, and sequences that form an epitope recognized by an available monoclonal antibody (e.g. 12CA5 monoclonal antibody) provide a binding site for the immobilized antibody.

Opiorph Receptor Antibodies

Antibodies that are specific for the opiorph receptor polypeptide(s) are provided. These antibodies may be polyclonal or monclonal, and may distinguish the opiorph receptor polypeptide(s) from other opioid receptors or other transmembrane proteins, discriminate opiorph receptor polypeptide (s) from different species, identify associational or other functional domains, and the like.

Such antibodies are conveniently made using the methods and compositions disclosed in Harlow and Lane, *Antibodies, A Laboratory Manual,* Cold Spring Harbor Laboratory, 1988, as well as immunological and hybridoma technologies known to those in the art.

Where natural or synthetic opiorph receptor-derived peptides are used to induce a specific immune response, the peptides may be conveniently coupled to an suitable carrier such as KLH and may be administered in a suitable adjuvant such as Freunds. Preferably, selected peptides are coupled to a lysine core carrier substantially according to the methods of Tam (1988) *Proc Natl Acad Sci USA* 85, 5409–5413. The resulting antibodies may be modified to a monovalent form, such as, for example, Fab, FAB', or FV. Anti-idiotypic antibodies, especially internal imaging anti-idiotypic antibodies, may also be prepared using known methods.

For example, purified opiorph receptor polypeptide(s) can be used to immunize mice. Subsequently, the mice spleens are removed. Splenocytes are used to form cell hybrids with myeloma cells and to obtain clones of antibody-secreted cells according to techniques that are known in the art. The resulting monoclonal antibodies are screened for their ability to bind immobilized opiorph receptor(s) or peptide fragments thereof.

In another example, peptides corresponding to different extracellular domains of the opiorph receptor polypeptide(s) are used as immunogens, and the resulting monoclonal antibodies are screened for their activity in inhibiting the binding of ligands to cells expressing the opiorph receptor polypeptide(s).

Anti-opiorph receptor polypeptide antibodies can be used to identify, isolate, and purify opiorph receptor polypeptide(s) from different sources and to perform subcellular and histochemical localization studies.

Applications

The polypeptides and nucleic acids sequences above can be used in the discovery, design, and development of pharmacologically useful opioid or opioid-like agonists and antagonists or unrelated non-opioid ligands. They can also be used in the design of diagnostic tests for pathological conditions influenced by the presence or absence of opiorph receptor polypeptide function.

For example, the cloned receptor polypeptide(s), or fragments thereof, can be expressed in a heterologous cell in which it can achieve a proper transmembrane orientation and an appropriate localization in the plasma membrane. Examples of suitable cells include COS cells, PC12 cells, CHO cells, Xenopus oocytes, and amphibian melanophore cells. The ability of the expressed polypeptide(s) to bind different ligands can be assessed either by measurement of binding of radiolabelled ligand directly using methods that are standard in the art followed by analysis by, for example, Scatchard analysis or by measurement of the ability of a ligand to alter forskolin-stimulated adenylate cyclase activity. For example, morphine (an exemplary opioid) inhibits the forskolin-stimulated adenylate cyclase activity of the rat or human mu-OR1 opioid receptor and also inhibits $IP_3$ production. Alternatively, in amphibian melanophore cells, a number of G-protein-regulated activities can be easily assessed by visually monitoring the effect of ligands on melanophore distribution within the cells (Jayawickreme, C. K. et al., (1994), *Proc.Natl.Acad.Sci. USA* 91:1614–1618).

In another embodiment, nucleic acid probes are prepared that are specific for the opiorph receptor polypeptide(s) and are used to measure the level of expression of opiorph receptor polypeptide mRNA in different tissues and under different physiological and/or pathological situations. The probes are labelled using a radioactive, fluorescent, or enzymatic label, and are used as direct hybridization probes in a Northern blot. Alternately, the probes can serve as primers for coupled reverse transcription-polymerase chain reaction, using RNA from the tissue as a template. This results in selective amplification of opiorph receptor related polynucleotide sequences only in tissues in which they are expressed.

Additionally, mutations can be introduced into the sequence of the opiorph receptor polypeptide(s). The mutated sequences are then expressed in a heterologous cell and the structure and function of the variants can be tested. Mutations in the predicted extracellular domains of the polypeptide should alter the opiorph receptor polypeptide(s) ability to bind ligands, while mutations in the predicted intracellular domains, including particular serine and threonine residues, will alter its ability to respond to ligand binding by initiating a biochemical signalling cascade within the cell.

DESCRIPTION OF THE PREFERRED EMBODIMENTS

The following examples illustrate the invention without limitation.

EXAMPLE 1

Cloning and Sequencing of Opiorph Receptor cDNA

A. Polymerase Chain Reaction

Two degenerate oligonucleotide primers were prepared using an automated oligonucleotide synthesizer. The first, 5'-ACGATGAA(GC)AC(TGA)GCCACCACCA-3' (SEQ ID NO: 7), was derived from the unique amino acid sequence VLVVVAVFIV (SEQ ID NO: 8) corresponding to amino acids 325–334 of the rat brain mu opioid receptor. The second primer, 5'-CTTCAA(TC)CTGGC(TC)TTGCCTGAT-3' (SEQ ID NO: 9), corresponds to amino acids 89–95 derived from the predicted second transmembrane domain, of the murine delta opioid receptor.

PCR reactions were carried out using rat genomic DNA as a template and the Taq polymerase PCR kit (Perkin-Elmer/Cetus, Inc.). The reactions included 20 ng of genomic DNA and 1 µg of each primer. The thermal cycling protocol was as follows: 94° C., 1 minute, followed by 35 cycles of 94.5° C., 20 seconds; 49° C., 45 seconds; 72° C., 45 seconds. This was followed by incubation at 72° C. for 10 minutes, after which the samples were placed on ice.

Resolution of the PCR products on a 1% agarose gel revealed the presence of products in the range of 500–600 bp in length.

The PCR products from the first reaction were then re-amplified, using identical primers and conditions as above. The products of the second PCR reaction were separated by electrophoresis in a 1% agarose gel, and discrete products were excised and purified on glass beads using the Gene-Clean kit (Bio-101). The purified fragments were then subcloned into the pCR-II vector (InVitrogen) and amplified in *E. coli*.

Bacterial colonies transformed with the pCR-II vector were subjected to alkaline lysis to isolate plasmid DNA. The DNAs were then sequenced using the dye primer automated sequencing system (Applied Biosystems, Model 373A). Sequence analyses and alignments were performed using the MacVector software package (I.B.I.).

This approach identified an unspliced opiorph receptor-encoding sequence corresponding to OR5 (see FIG. 3). This sequence contains the 84 nucleotides that are absent from the smaller splice variant.

B. Library screening pPCR4A is a 700 base pair (bp) pPCRII (InVitrogen) subclone of a partial mu opiate receptor cDNA amplified from single stranded rat brain cDNA. The 700 bp pPCR4A insert was excised with EcoRI, radiolabelled by random priming, and used to isolate cDNAs from a size-selected rate cerebral cortex lambda ZAP cDNA library. Sequence analyses of the inserts from autoexcised plasmids revealed apparent partial sequences with substantial homology to other cloned opiate receptors, including a 2.8 kb cDNA, from which a 5' 500 bp fragment was isolated using HindIII. This fragment was radiolabeled by random priming and was used to isolate other more 5' cDNAs including a 3 kb cDNA. Inserts from the two clones were cut and ligated to form a fused clone encoding the smaller, splice-variant form of the opiorph receptor (SEQ ID NO: 2) i.e. lacking the internal 28 amino acids encoded by the spliced-out oligonucleotide (SEQ ID NO: 6) (see FIG. 3).

The present cDNAs add substantially to the diversity of the gene subfamily that contains opiate receptors. The splice variant documented for this receptor represents the first example of differential splicing in this receptor gene subfamily, and suggests an intron-exon border likely to be conserved in several opiate receptor subfamily genes.

EXAMPLE 2

Tissue Distribution of Opiorph Receptor MRNA

A. Reverse Transcription-Polymerase Chain Reaction

Two oligonucleotide primers were prepared corresponding to nucleotides 417 to 438 and 828 to 849 of the sequence of FIG. 1 (SEQ ID NO: 1), consisting of 5'-AGGGCACAGACATCCTACTGG-3' (SEQ ID NO: 10) and 5'-AGCCTGAAAGCAGACGGACAC-3' (SEQ ID NO: 11).

RNA was prepared from rat tissues that were rapidly dissected and frozen at −70° C. and from rat cell lines. The RNAs served as templates for combined reverse-transcriptase-polymerase chain reactions (RT-PCR). The reactions were carried out using an RT-PCR kit (Perkin-Elmer/Cetus) employing rTth bifunctional polymerase. Synthesis of single-stranded cDNA was performed using 100–200 ng of RNA and 2 μg of the 3′ primer. After incubation at 65° C. for 10 minutes, chelating buffers, $MgCl_2$, and 0.75 μg of the 5′ primer were added. The thermal cycling sequence was as follows: 94° C., 1 minute, followed by 35 cycles of 94.5° C., 20 seconds; 60° C., 20 seconds; and 72° C., 60 seconds. The reaction mixtures were then chilled, and the products were analyzed on a 1% agarose gel in tris-borate-EDTA buffer.

Figure 5:
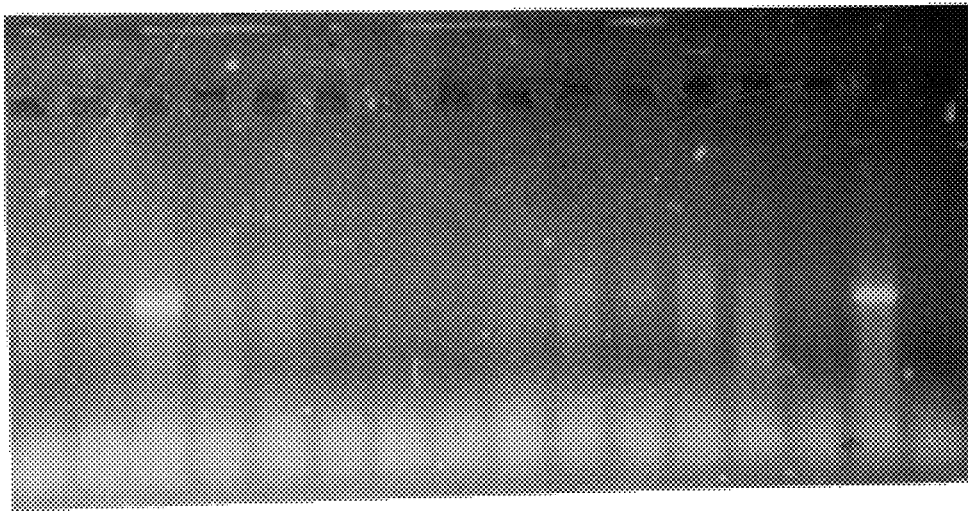
FIG. 5 is an illustration of an autoradiogram showing the tissue distribution of mRNA encoding an opiorph receptor polypeptide, as determined by reverse transcription-polymerase chain reaction (RT-PCR) using, as a template, RNA derived from different rat tissues and cell lines. The RT-PCR products were resolved in an agarose gel. The left lane contains molecular mass markers, after which the lanes are numbered sequentially 1–16 from left to right.

Results are shown in FIG. 5 and indicate that opiorph receptor is expressed in brain, pituitary, thymus, stomach, muscle, and fat tissues.

In another experiment, reverse transcription-PCR was performed using as template 5 μg of total RNA extracted from different tissues and oligonucleotide primers 5′-ACCCTGGTCTTGCTAACA-3′ (SEQ ID NO: 12) and 5′-CAGCACCAGTCGAGTGAT-3′ (SEQ ID NO: 13). Single-stranded cDNA was amplified by 35 cycles of 94° C. for 1 minute, 55° C. for 1 minute, and 92° C. for 1 minute), with separation of PCR products by 2% agarose gel electrophoresis, transfer to nylon membranes, hybridization overnight with a $^{32}$P-labeled opiorph cDNA probe at 42° C., followed by phosphorimaging.

Figure 6A:
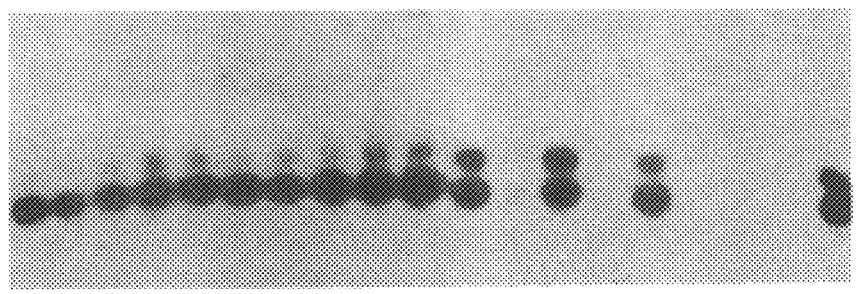
FIG. 6A is an illustration of an autoradiogram showing the tissue distribution of mRNA encoding an opiorph receptor polypeptide, as determined by RT-PCR using as a template RNA derived from different rat tissues. The RT-PCR products were resolved in an agarose gel, transferred to nylon membranes, and hybridized with an opiorph receptor polypeptide-specific radiolabelled DNA probe. The tissues used as sources of RNA were as follows: Lane 1, cerebellum; lane 2, cerebral cortex; lane 3, striatum; lane 4, midbrain; lane 5, hippocampus; lane 6, brainstem; lane 7, olfactory bulb; lane 8, spinal cord; lane 9, thalamus; lane 10, hypothalamus; lane 11, intestine; lane 12, skeletal muscle; lane 13, vas deferens; lane 14, esophagus; lane 15, liver; lane 16, kidney; lane 17, testis; lane 18, adrenal; and lane 19, spleen.
Figure 6B:
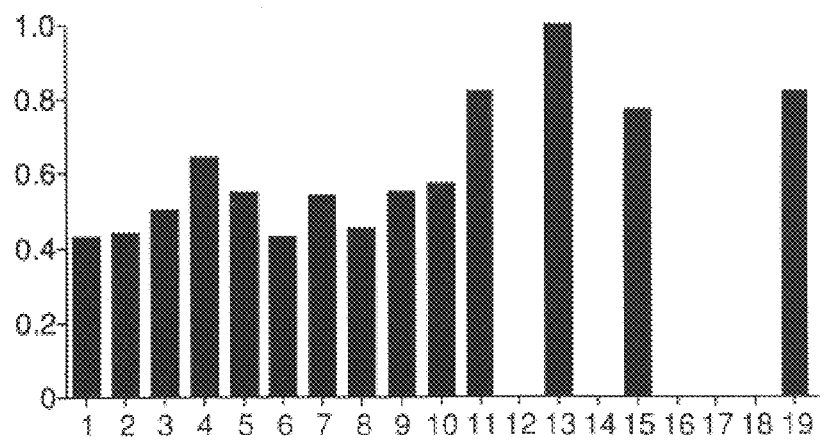
FIG. 6B is an illustration of the ratio between the RT-PCR products derived from the small and large splice variants, respectively. The tissues are as in FIG. 6A. The Y-axis represents the ratio of labelled hybridization probe recognizing the short variant to that recognizing the long variant.

Results are shown in FIGS. 6A and 6B. FIG. 6A indicates that two splice variant products were detected in various brain regions, as well as in several peripheral tissues such as intestine, skeletal muscle, vas deferens and spleen. FIG. 6B indicates that the ratio between the two splice variants also varies among the brain regions and peripheral tissues examined.

B. Northern Analysis

Total RNA was prepared from rat tissues that were rapidly dissected and frozen at −70° C. 20 μg of each RNA were resolved in agarose-formamide gels. The separated RNA species were then transferred to nylon membranes. Blots were hybridized with opiorph receptor cDNA radiolabelled with $^{32}$p by random priming. Hybridizations were carried out in 50% formamide, 5× SSC, 50 mM $NaPO_4$, 1% SDS, 2.5× Denhardt's solution, and 200 μg/ml salnon sperm DNA at 42° C. overnight. The filters were then washed twice in 0.1× SSC/0.1% SDS for 30 minutes at 65° C. Radioactive patterns were identified using a phosphorimaging device (Molecular Dynamics) following overnight exposures.

Figure 7:
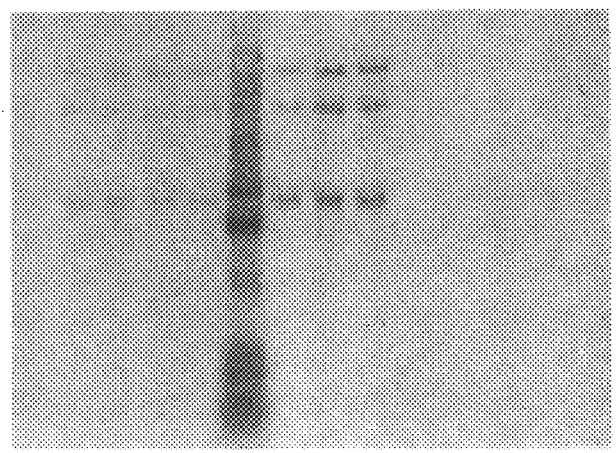
FIG. 7 is an illustration of a Northern blot of RNA derived from rat thalamus (TH, lanes 11–4), hypothalamus (HV, lanes 5–8), and striatum (ST, lanes 9–12) hybridized to a radiolabelled opiorph receptor polypeptide DNA probe.

Results are illustrated in FIG. 7. This analysis revealed that the highest levels of opiorph receptor expression are in the hypothalamus. At least three hybridizing mRNA species are observed in this brain region and in brainstem, midbrain, cerebral cortex, thalamus and hippocampus, but not in striatum or cerebellum.

Conceivably, two of these three mRNAs could represent products of different genes closely related to OR7 in sequence. Alternately, mRNA splicing and/or polyadenylation site usage events in the gene's untranslated regions could yield the significant differences in transcript molecular mass noted in Northern analyses.

EXAMPLE 3

Heterologous Expression of Opiorph Receptor in COS cells

COS cells were transfected by electroporation with 20 μg/$10^7$ cells of opiorph cDNA which had been cloned into the pcDNAI vector (InVitrogen). Transfected cells were plated in Dulbecco's modified minimal essential medium (GIBCO, Grand Island, N.Y.) containing 10% fetal bovine serum and maintained at 37° C. in a humidified atmosphere containing 5% $Co_2$.

Expression of opiorph receptor polypeptide(s) was assessed by measurement of specific ligand binding. Alternatively, expression of opiorph receptor polypeptide(s) may be assessed by RNA extraction and RT-PCR according to the procedure of Example 2 above or immuno assay with antibodies specific to the opiorph receptor(s).

EXAMPLE 4

Analysis of Ligand Binding Characteristics of Opiorph Receptors

COS cells transfected with opiorph receptor cDNA or, as a control, rat or human mu opiate receptor cDNA were harvested. Membranes were prepared by homogenization at 4° C. in 50 mM Tris buffer and centrifugation at 1000×g for 10 minutes. The supernatant was then recovered and subjected to centrifugation at 46,000×g for 30 minutes. The membrane-containing pellet was recovered, and fractions corresponding to 50 μg of protein were resuspended in 0.5 ml of Tris buffer and incubated with different radiolabelled ligands.

The ligands were: [$^3$H]bremazocine (29.2 Ci/mmol, NEN), [$^3$H]naloxone (47.2 Ci/mmol, NEN), [$^3$H] diprenorphine (29 Ci/mmol, NEN), [$^3$H]DAMGO ([D-Ala2, N-Methyl-Phe4,Glyol[5]enkephalin; 60 Ci/mmol, Amersham), [$^3$H]DPDPEpCl ([D-Pen2,4′-Cl-Phe4,D-Pea5] enkephalin; 51 Ci/mmol, NEN), [$^3$H]DADLE (D-Ala2,D-Leu5 enkephalin; 37 Ci/mmol, NEN), [$^3$H] ethylketocyclazocine (28.5 Ci/mmol, NEN), [$^3$H]etorphine (38.7 Ci/mmol, NEN), [$^3$H]buprenorphine (13.4 Ci/mmol, RBI). [$^{125}$I]β-endorphin (2,000 Ci/mmol, Amersham) and [$^3$H]U-69,593 (57 Ci/mmol, Amersham).

Incubations were for 150 minutes at 22° C., after which the reactions were filtered through GFB filters (Whatman). The filters were washed three times with Tris buffer at 4° C. Radioactivity associated with the filters was determined by liquid scintillation counting, and data were analyzed using EBDA and LIGAND (Munson et al., *Anal. Biochem.* 107:220, 1980).

Under conditions in which robust binding to rat or human μOR1 polypeptides was observed, no definitive binding of the above ligands to opiorph receptor polypeptide(s) was observed. No specific radioligand binding above background levels was observed in eight of ten experiments using cells expressing the smaller splice variant of the opiorph receptor or in four of four experiments using cells expressing the larger splice variant. In two experiments, modest naloxone-displacable diprenorphine, bremazocine, and β-endorphin binding above background values was noted in cells expressing the smaller splice variant. However, intermittent naloxone-displacable binding of naloxone and β-endorphin was also observed in mock-transfected COS cells in several negative control experiments. Neither radiolabeled diprenorphine, bremazocine, not β-endorphin displayed specific binding in eight additional experiments. Neither ethylketocyclazocine, naloxone, DAMGO, DPDPE, U,69,693, ctorphine, buprenorphine, not DADLE resulted in specific binding in any experiment.

COS cells transfected with either the large or small splice variant of OR7 failed to display consistent opiate-induced alteration in forskolin-stimulated adenylate cyclase activity.

In 14 experiments in which morphine-inhibited adenylate cyclase activity in COS cells expressing rat or human mu opiate receptor cDNAs served as positive controls, eight of 10 experiments revealed no opiate-mediated inhibition of forskolin-stimulated cyclase activity in cells expressing the smaller splice variant of OR7, and four of four experiments revealed no opiate-mediated inhibition of forskolin-stimulated cyclase activity in cells expressing the larger splice variant of OR7. In two experiments, bremazocine, buprenorphine, etorphine and β-endorphin did elicit modest naloxone-reversible inhibition of forskolin-stimulated cyclase activity in cells expressing the smaller splice variant. However, intermittent naloxone-reversible β-endorphin effects were also noted in some experiments in mock-transfected cells. Neither bremazocine, buprenorphine, etorphine nor endorphin altered forskolin-stimulated cA-MP levels in eight additional experiments; neither DADLE, Dynorphin A, morphine, nor U50,488 altered cAMP levels in any experiment.

Deposit of Biological Materials

The following biological materials were deposited with the American type Culture Collection, 12301 Park Lain Drive, Rockville, Md. 20857 as follows:

Strain OZ86 deposited Dec. 23, 1993,

Accession Number ATCC 69525.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

We claim:

1. An isolated polypeptide consisting of amino acids 88–269 of SEQ ID NO:2 prepared by a method comprising the steps of:

(a) culturing a host cell in a medium and under conditions suitable for expression of said polypeptide, said host cell comprising a vector capable of directing the expression of said polypeptide in said host cell, wherein said vector comprises a DNA sequence which encodes said polypeptide, wherein said DNA sequence consists of nucleotides 368 to 913 of SEQ ID NO:1;

(b) expressing said polypeptide; and (c) isolating said expressed polypeptide.

2. An isolated polypeptide consisting of amino acids 88–269 of SEQ ID NO:2 prepared by a method comprising the steps of:

(a) culturing a host cell in a medium and under conditions suitable for expression of said polypeptide, said host cell comprising a vector capable of directing the expression of said polypeptide in said host cell, wherein said vector comprises a DNA sequence consisting of nucleotides which encode amino acids 88–269 of SEQ ID NO:2;

(b) expressing said polypeptide; and (c) isolating said expressed polypeptide.

3. An isolated polypeptide consisting of amino acid residues 88–269 of SEQ ID NO:2.

* * * * *